(12) United States Patent
Venturi (10) Patent No.: US 12,409,264 B2
(45) Date of Patent: Sep. 9, 2025

(54) ADIPOSE TISSUE SEPARATION DEVICE WITH PRESSURE EQUALIZATION

(71) Applicant: Mark Louis Venturi, Washington, DC (US)

(72) Inventor: Mark Louis Venturi, Washington, DC (US)

(*) Notice: Subject to any disclaimer, the term of this patent is extended or adjusted under 35 U.S.C. 154(b) by 0 days.

(21) Appl. No.: 18/917,987

(22) Filed: Oct. 16, 2024

(65) Prior Publication Data

US 2025/0121125 A1    Apr. 17, 2025

Related U.S. Application Data (60) Provisional application No. 63/590,721, filed on Oct. 16, 2023.

(51) Int. Cl.
*A61M 1/00*    (2006.01)

(52) U.S. Cl.
CPC .............. *A61M 1/892* (2021.05); *A61M 1/60* (2021.05)

(58) Field of Classification Search
CPC .... A61B 10/02; A61B 10/0045; C12M 45/02; C12M 47/02; C12M 47/04; C12M 45/09; A61M 2202/08; A61M 1/79; A61M 1/892; A61M 1/60; A61M 1/63; A61M 1/88; A61M 2205/7545; A61M 1/3695; A61M 1/89; A61M 1/895; A61M 1/81; A61M 2202/0014; A61M 2202/0021; A61M 2202/09; A61M 1/631; A61M 1/67; A61M 1/782

See application file for complete search history.

(56) References Cited

U.S. PATENT DOCUMENTS

| | | |
|---|---|---|
| 975,314 A | 11/1910 | Baker |
| 1,009,664 A | 11/1911 | Hefty et al. |
| 1,731,409 A | 10/1929 | Fitts |
| 3,204,864 A | 9/1965 | Malaker et al. |
| 4,870,975 A | 10/1989 | Cronk et al. |
| 5,409,833 A | 4/1995 | Hu et al. |
| 5,624,418 A | 4/1997 | Shepard |

(Continued)

OTHER PUBLICATIONS

Examination Report No. 1 dated Jan. 10, 2018, directed to AU Application No. 2016268235; 3 pages.
Examination Report No. 2 dated Dec. 24, 2018, directed to AU Application No. 2016268235; 3 pages.
Examination Report No. 3 dated Jan. 8, 2019, directed to AU Application No. 2016268235; 3 pages.

(Continued)

*Primary Examiner* — Kai H Weng
(74) *Attorney, Agent, or Firm* — PK Patent Law (57) ABSTRACT

A tissue separating device and a method of separating pure fat are provided. The tissue separating device includes a canister device including canister body having a sidewall defining a volume. A tissue retrieval port can be arranged on the canister device and arranged in fluid communication with a harvesting device for directing a fatty liposuction aspirate into the canister device. An adjustable height filtration assembly can be arranged within the canister body. A tissue harvesting port can be arranged in the sidewall of the canister body and can be in communication with a collection device to allow the tissue harvesting port to atraumatically receive a filtered pure fat. An air pressure equalizing line can be operatively mounted to the canister device to allow fluid connection between the upper vacuum chamber and the lower vacuum chamber. The filtration assembly can be movably arranged within the canister body.

20 Claims, 4 Drawing Sheets

(56) References Cited

U.S. PATENT DOCUMENTS

| | | | |
|---|---|---|---|
| 7,192,518 | B2 | 3/2007 | Roesgen |
| 7,758,556 | B2 | 7/2010 | Perez-Cruet et al. |
| 8,048,046 | B2 | 11/2011 | Hudspeth et al. |
| 8,100,874 | B1 | 1/2012 | Jordan et al. |
| 8,172,832 | B1 | 5/2012 | Gonzalez |
| 8,361,042 | B1 | 1/2013 | Gonzalez |
| 8,366,694 | B1 | 2/2013 | Jordan |
| 8,845,605 | B2 | 9/2014 | Hensler et al. |
| 8,858,518 | B2 | 10/2014 | Schafer et al. |
| 9,192,939 | B2 | 11/2015 | Tremolada |
| 9,248,384 | B2 | 2/2016 | Dominguez et al. |
| 9,358,327 | B1 | 6/2016 | Venturi |
| 9,565,965 | B2 | 2/2017 | De Petra et al. |
| 10,406,265 | B2 | 9/2019 | Kensy et al. |
| 10,874,777 | B2 | 12/2020 | Venturi |
| 2004/0097867 | A1* | 5/2004 | Fraser .................... C12M 47/04 604/27 |
| 2012/0271254 | A1* | 10/2012 | Schafer ................ A61M 1/895 604/319 |
| 2018/0117223 | A1* | 5/2018 | Venturi .................. A61M 1/88 |

OTHER PUBLICATIONS

Extended European Search Report dated Oct. 23, 2018, directed to EP Application No. 16800629.4; 7 pages.

International Preliminary Report on Patentability dated Nov. 28, 2017, directed to International Application No. PCT/US2016/033896; 12 pages.

International Search Report and Written Opinion dated Sep. 12, 2016, directed to International Application No. PCT/US2016/033896; 14 pages.

Notice of Acceptance dated Jan. 10, 2019, directed to AU Application No. 2016268235; 3 pages.

Search Report and Written Opinion dated Mar. 12, 2020, directed to BR Application No. BR112017024457-8; 4 pages.

Venturi, U.S. Notice of Allowance and Fee(s) Due dated May 2, 2016, directed to U.S. Appl. No. 14/723,717; 7 pages.

Venturi, U.S. Office Action dated Dec. 24, 2015, directed to U.S. Appl. No. 14/123,717; 13 pages.

Examination Report No. 1 dated May 29, 2020, directed to AU Application No. 2019202718; 6 pages.

* cited by examiner

ADIPOSE TISSUE SEPARATION DEVICE WITH PRESSURE EQUALIZATION

CROSS REFERENCE TO RELATED APPLICATION

The present application claims the benefit from earlier filed U.S. Provisional Patent Application No. 63/590,721, filed Oct. 16, 2023, which is incorporated herein in its entirety by reference.

FIELD OF THE INVENTION

The present teachings relate to a tissue separating device for body fluids and tissue specimens. In particular, the present teachings relate to a separation device for use with a suction source to withdraw and separate body fluids and tissue specimens from a patient in an atraumatic manner.

BACKGROUND OF THE INVENTION

Autologous adipose tissue (or fatty tissue) transplantation is performed by many surgeons for various cosmetic and reconstructive procedures. Autologous fat transplantation involves retrieving adipose tissue using liposuction techniques from an area of abundance and then re-injecting the harvested adipose tissue into a different site of the same individual for cosmetic/reconstructive augmentation or enhancement purposes. Generally, prior to the re-introduction of the tissue into the patient, the adipose tissue must be processed or cleaned to maximize the chances of implant survival. Such processing is preferably accomplished while minimizing the exposure of the tissue to air as much as possible. However, the adipose cells arc relatively delicate and the number of steps and length of time required to separate and process the harvested tissue prior to re-introduction into the patient contributes directly to the success of the operation and decreases the likelihood the tissue will be rejected.

However, the nature of liposuction procedures preclude easy tissue isolation after initial harvest, especially on a large scale, because the volume and/or viscosity of the extracted liposuction effluent also contains unwanted components such as oil, blood and anesthetic solution. Currently, there are no standard techniques, methods, or devices that exist for the simple, large scale isolation and refinement of liposuction-harvested adipose tissue. Although a number of specialized cannulas, needles and methods for tissue harvest and preparation exist, these techniques are tedious and inefficient. Often, the harvested fat is introduced into a centrifuge further traumatizing the fat and adding more steps to the process before the adipose tissue is re-injected back into the patient. As a result, centrifuge-free processes have been developed.

Known centrifuge-free processes require a large number of steps which result in a cumbersome harvesting and re-injection process that leaves room for much improvement.

Accordingly, there exists a need for an efficient, simple-to-use, low-cost to manufacture and assemble tissue collection and processing device that reduces the trauma to harvested tissue, improves the amount of useful tissue, and maintains a sterile processing environment.

SUMMARY OF THE INVENTION

The present teachings provide a tissue separating device including a canister device including a canister body having a sidewall defining a volume. A tissue retrieval port can be arranged on the canister device and can be capable of being arranged in fluid communication with a harvesting device for directing a fatty liposuction aspirate into the volume of the canister device. An adjustable height filtration assembly can be arranged within the canister body and can include a filtering material separating the volume into an upper vacuum chamber and a lower vacuum chamber. A tissue harvesting port can be arranged in the sidewall of the canister body and can be capable of being arranged in communication with a collection device to allow the tissue harvesting port to atraumatically receive a filtered pure fat collected on the filtering material within the upper vacuum chamber. An air pressure equalizing line can be operatively mounted to the canister device to allow fluid connection between the upper vacuum chamber and the lower vacuum chamber. The filtration assembly can be movably arranged within the canister body such that the filtering material can be adjustable with respect to the tissue harvesting port.

The present teachings also provide a tissue separating device including a canister device including a canister body having a sidewall defining a volume. An adjustable height filtration assembly can be arranged within the canister body and can include a filtering material having a top side portion and a bottom side portion. The filtering material can separate the volume into an upper vacuum chamber and a lower vacuum chamber. A tissue retrieval port can be arranged on the canister device and can be capable of being arranged in fluid communication with a harvesting device for directing a fatty liposuction aspirate into the-volume of the canister device onto the top side portion of the filtering material. An air pressure equalizing line can be operatively mounted to the canister device to allow fluid connection between the upper vacuum chamber and the lower vacuum chamber. A tissue harvesting port can be arranged in the sidewall of the canister body and can be capable of being arranged in communication with a collection device for atraumatically receiving a filtered pure fat component collected on the top side portion of the filtering material. The adjustable height filtration assembly can be movably arranged within the canister body such that the filtering material is adjustable with respect to the tissue harvesting port.

The present teachings still further provide a tissue separating device including a canister device including a canister body having a sidewall defining a volume. A tissue retrieval port can be arranged on the canister device and can be capable of being arranged in fluid communication with a harvesting device for directing a fatty liposuction aspirate into the volume of the canister device. A single adjustable height filtration assembly can be arranged within the canister body and can include a filtering material separating the volume into an upper vacuum chamber and a lower vacuum chamber such that the fatty liposuction aspirate can be directed by the tissue retrieval port into the upper vacuum chamber. A tissue harvesting port can be arranged in the sidewall of the canister body and can be capable of being arranged in communication with a collection device to allow the tissue harvesting port to atraumatically receive a filtered pure fat collected on the filtering material within the upper vacuum chamber. A vacuum connector can be provided for creating a vacuum in the upper vacuum chamber. The vacuum connector and the tissue retrieval port can be arranged on the same side of the filtering material so that vacuum is applied on the same side of the filtering material as the upper chamber. An air pressure equalizing line can be operatively mounted to the canister device to allow fluid connection between the upper vacuum chamber and the lower vacuum chamber.

The present teachings further provide a method of separating pure fat from a fatty liposuction aspirate. The method includes providing a canister device defining a volume, the canister device including a tissue retrieval port, a filtration assembly including a filtering material having a top side portion and a bottom side portion and being movably arranged within the canister body, and a tissue harvesting port. The method then directs a fatty liposuction aspirate into the volume of the canister device and onto the top side portion of the filtering material of the filtration assembly. The method then separates the fatty liposuction aspirate using the filtering material into a filtered pure fat component collected on the top side portion of the filtering material and into an aqueous fluid component collected below the filtering material. The method includes moving the filtering material with respect to the tissue harvesting port into a position to place the separated pure fat collected on the top side portion of the filtering material in communication with a collection device. The method can include equalizing an air pressure between the upper vacuum chamber and the lower vacuum chamber, as well as creating a vacuum at the tissue harvesting port using the collection device to atraumatically remove the filtered pure fat from the canister body without manipulating the fat.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Figure 1:
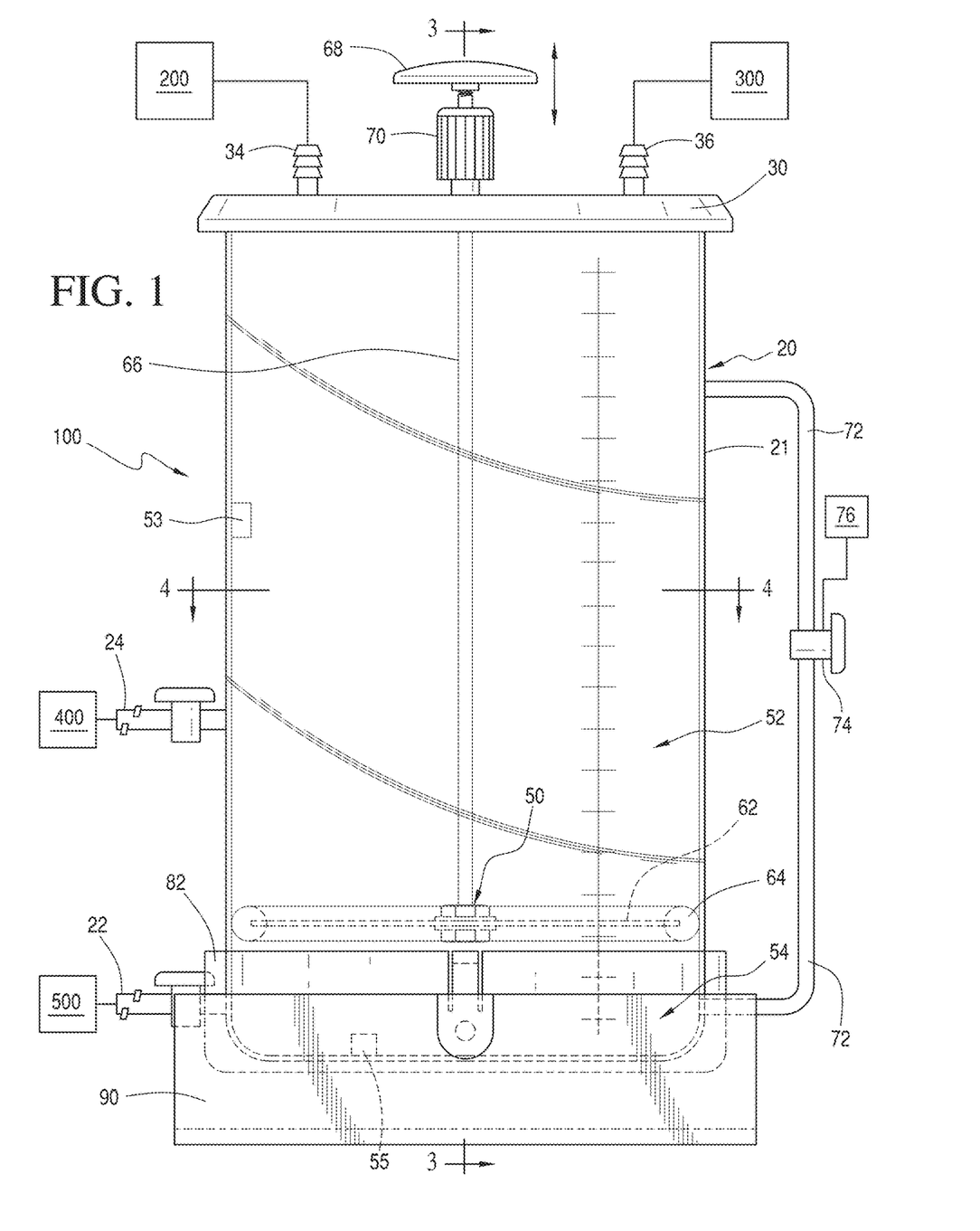
FIG. 1 shows a side view of the tissue separating device of the present teachings.

Referring to at least FIG. 1, a tissue separating device 100 in accordance with a preferred embodiment of the present teachings is shown. The tissue separating device 100 can include a canister device 20 including a canister body 21 and a lid 30. The canister device 20 can include a vacuum connector 34 and a tissue retrieval port 36 which can be arranged in the lid 30. The vacuum connector 34 can be operatively coupled to a vacuum source 200 via tubing. The tissue retrieval port 36 can be operatively coupled to a harvesting device 300 via a liposuction cannula. A sidewall of the canister body 21 can include a fluid evacuation port 22 and a tissue harvesting port 24. The tissue separating device 100 can also include an adjustable height filtration assembly 50 that is operable to divide the interior of the canister device 20 into an upper vacuum chamber 52 and a lower vacuum chamber 54.

In use, a quantity of fatty liposuction aspirate can be directed into the canister device 20 through the tissue retrieval port 36 when a suction or negative pressure is applied to the sterile interior chamber of the canister device 20. The suction pressure can be created by connecting the vacuum source 200 to the vacuum connector 34. The fatty liposuction aspirate is directed into the upper vacuum chamber 52 and becomes filtered by the adjustable height filtration assembly 50 by way of gravity. The filtering material 62 of the filtration assembly 50 can separates pure fat from the aqueous component of the fatty liposuction aspirate. The filtered pure fat remains on the upper vacuum chamber 52 side of the filtration assembly 50 while the aqueous component of the fatty liposuction aspirate is collected at the bottom of the canister body 21 below the filtration assembly 50. The filtering material 62 of the filtration assembly 50 can be a mesh or mesh-like material.

As will be discussed in more detail below, the filtering material 62 of the filtration assembly 50 can be moved up and down the sidewall 28 of the canister body 21 and can be set at any height to facilitate the atraumatic removal of pure fat from the canister device 20 without manipulating the fat. The pure fat can be removed through the tissue harvesting port 24 by way of a collection syringe 400 or other collection mechanism. The pure fat can then be re-injected by the surgeon for fat grafting purposes. The remaining aqueous fluid component collected below the filtration assembly 50 can be separately aspirated from the canister device 20 through the fluid evacuation port 22 into a different collection syringe 500 or other collection mechanism.

The tissue separating device 100 of the present teachings can be used as part of a larger tissue retrieval system. For example, the tissue separating device 100, when operatively placed in communication with other components such as a vacuum source 200, a waste canister (not shown), collection syringes 400, 500, tissue harvesting devices 300, and others using associated conduits and tubing, can be part of a high volume, sterile, closed environment system. The system can facilitate the harvesting of aspirated, adipose tissue, and the tissue separating device 100 of the present teachings can be used to separate such tissue from other collected tumescent fluids, oils, blood, and anesthetics. As will be discussed in more detail below, pre-loading the canister device 20 with a fluid bath can be implemented to further reduce the trauma to the harvested tissue and contribute to the refining process.

Figure 3:
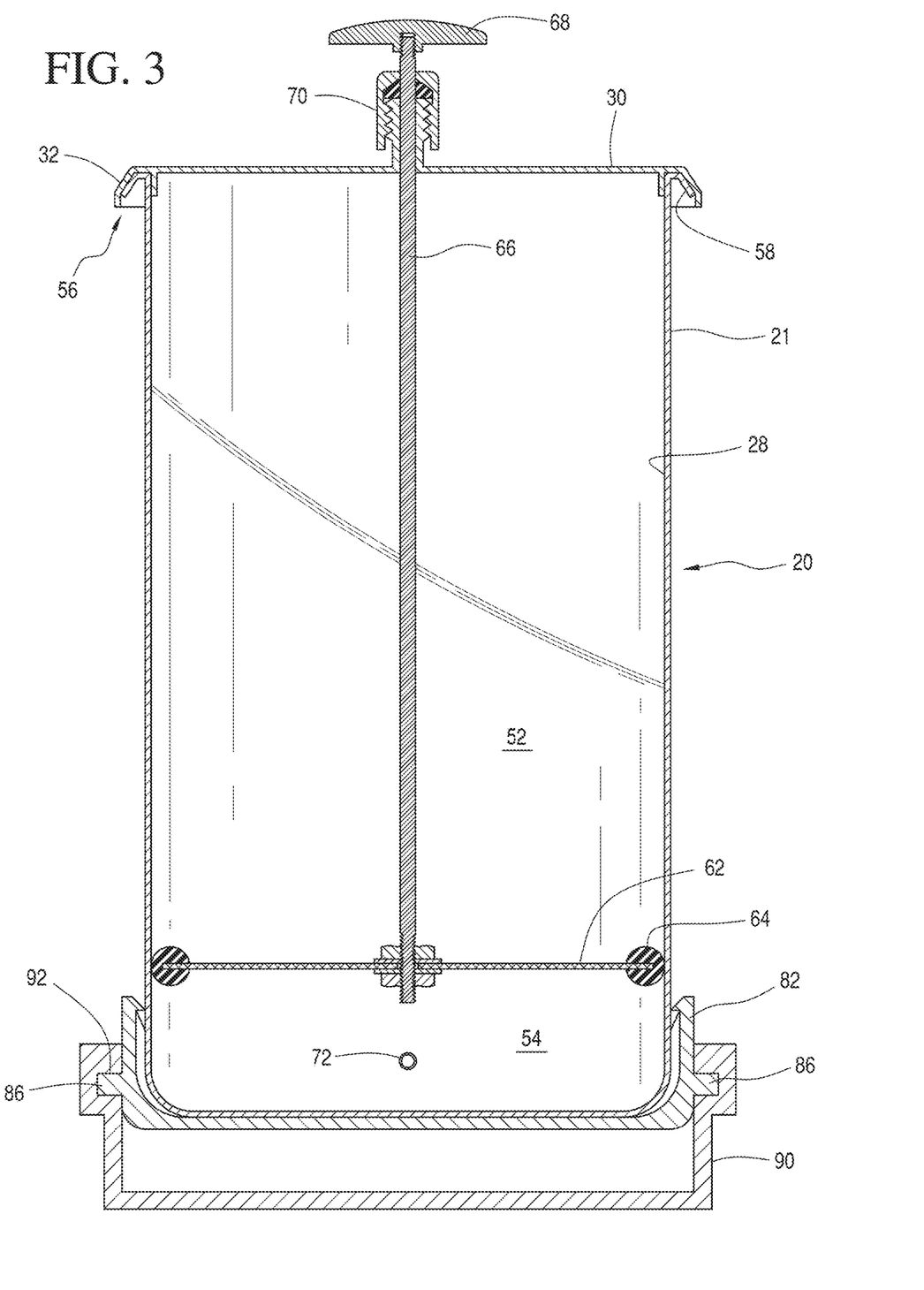
FIG. 3 shows a side cross-sectional view of the tissue separating device taken through line 3-3 of FIG. 1.
Figure 4:
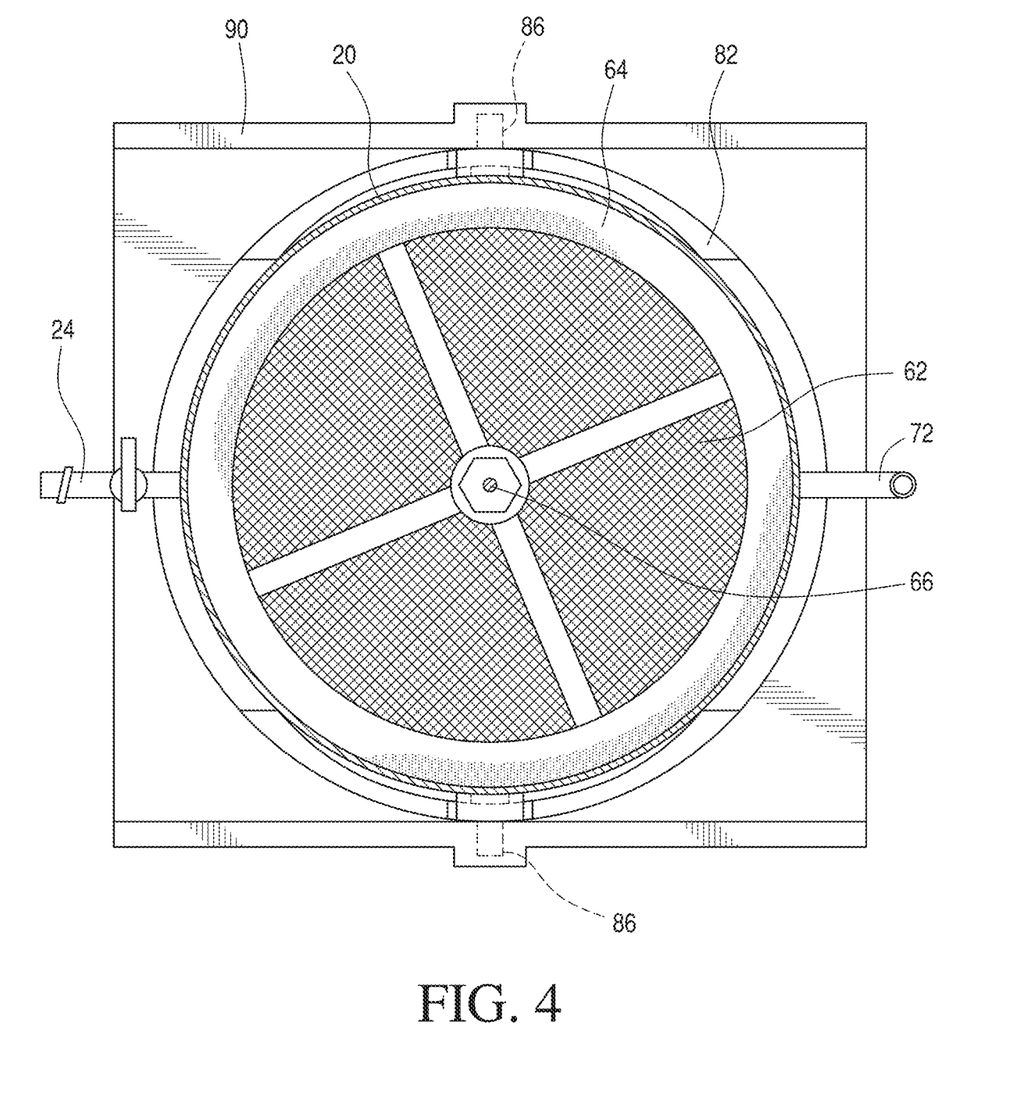
FIG. 4 shows a top view of the tissue separating device taken through line 4-4 of FIG. 1.

Referring now to FIG. 3, the canister body 21 can include a generally cylindrically shaped sidewall 28 that can terminate in an upper rim 56 with an outwardly projecting flange 58 surrounding an open top that preferably faces upwardly when in use. The upper rim 56 forms an attachment surface for a removable lid 30 as will be described in more detail below. According to various embodiments, the removable lid 30 can include various shapes and sizes and could be formed in a hinged relationship with the canister body 21.

According to various embodiments, the canister body 21 can have a capacity from about 100 ml to about 4 liters. However, it has been found that a canister capacity of from about 1.2 liters to about 2.0 liters has been found to be suitable for most autologous adipose tissue re-injection procedures. However, these size ranges are not meant to be limiting in any manner and other suitable smaller or larger capacities as dictated by the procedure to be performed would be appreciated by one of ordinary skill in the art.

Figure 2:
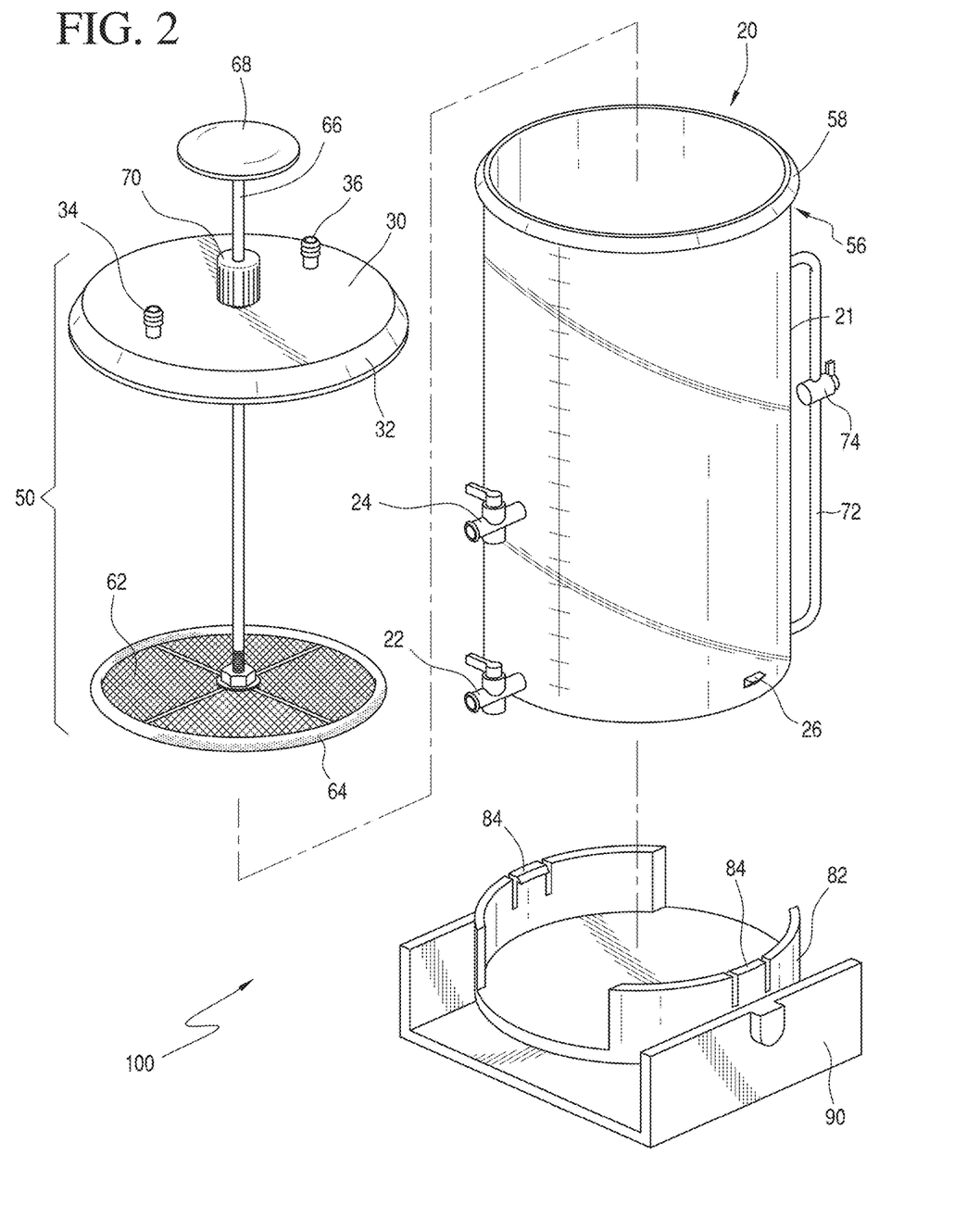
FIG. 2 shows a perspective exploded view of the tissue separating device of the present teachings.

As best shown in FIGS. 2 and 3, the adjustable height filtration assembly 50 can include a filtering mesh 62 having a resilient O-ring 64 arranged about its circumference to prevent fluid from passing between the filtering mesh 62 and an interior surface of the sidewall 28 of the canister body 21. The filtering mesh 62 can span the interior diameter of the canister body 22 and effectively form a perforated separation between the upper vacuum chamber 52 and the lower vacuum chamber 54.

The height of the filtering material 62 within the canister body 21 can be arranged to be selectively adjustable. The filtering material 62 can be secured to a movable rod 66 which extends through an aperture in the lid 30. A top end portion of the movable rod 66 can include a handle 68 that allows a user to grasp the rod 66 and adjust the height of the filtering material 62 within the canister body 21. The movable rod 66 and filtering material 62 can be held in place at any particular height within the canister body 21 by way of any type of locking, gripping, or holding mechanism 70. For example, the movable rod 66 can be secured at any height using a gasket arrangement 70 that provides a friction fit between the movable rod 66 and the lid 30. For another example, the movable rod 66 can be arranged in threaded engagement with the lid 30 allowing concise height adjustment by turning the handle 68.

The filtering material 62 of the filtration assembly 50 can be moved up and down the canister body 21 and can be secured at any particular height within the canister body 21. In particular, the height of the filtering material 62 of the filtration assembly 50 can be set at any location below the tissue harvesting port 24. The adjustment of the filtering material 62 allows the surgeon to indirectly manipulate the filtered pure fat that has accumulated on the upper vacuum chamber 52 side of the filtering material 62 towards the tissue harvesting port 24. Thus, the height adjustable filtration assembly 50 facilitates the atraumatic removal of pure fat from the canister device 20 without manipulating the fat.

The perforations in the filtering material 62 are sized to allow fluids such as oils, free lipids, tumescent fluids, non-fatty tissues, blood, anesthetic fluids, and saline gathered during the harvesting process or introduced into the canister device 20 to drain from the upper vacuum chamber 52 to the lower vacuum chamber 54. At the same time, the perforations in the filtering material 62 are sized to restrict the passage of adipose tissue. A preferable aperture size of about 1.0 mm has been determined to be suitable for the desired flow rate while avoiding clogging issues but other suitable sizes, including, but not limited to an aperture size range of about 0.2 mm to about 2.0 mm, depending on the tissue being collected, quantity desired, and desired pass through rate without undue clogging will occur to one of ordinary skill in the art.

While a single filtering material 62 is shown in this embodiment, additional filtering materials could be implemented as part of the filtration assembly 50. Depending on the vacuum strength introduced by the vacuum source 200, some of the fatty tissue may pass through the filtering material 62 or lodge into the perforations of the material 62. However, clogging is generally avoided since the fatty tissue tends to float and only settles onto the filtering material 62 once all other fluids in the fatty liposuction aspirate have been evacuated through the perforations and into the lower vacuum chamber 54. While the filtering material 62 is preferably constructed of a mesh material, other suitable filtering materials could be implemented as would be appreciated by one of ordinary skill in the art.

As best shown in FIGS. 1 and 2, an air pressure equalizing line 72 can be operatively mounted to the canister body 21 such that an upper end of the air pressure equalizing line 72 can fluidically connect with the upper vacuum chamber 52 and a lower end can connect with the lower vacuum chamber 54 at a location below the filtering material 62. Fluid flow through the air pressure equalizing line 72 can be controlled by any fluid flow control mechanism 74, such as a stop cock valve.

The valve 74 can be arranged to equalize the air pressure manually or automatically between the upper vacuum chamber 52 and the lower vacuum chamber 54.

According to various embodiments, the valve 74 can be controlled via an electrical controller 76 and pressure sensors 53, 55 arranged in each of the upper vacuum chamber 52 and the lower vacuum chamber 54. The electrical controller 76 can be used to automatically equalize the air pressure between the upper vacuum chamber 52 and the lower vacuum chamber 54 using pressure readings from the pressure sensors 53, 55.

If the filtering material 62 becomes partially or fully clogged during use and the filtration assembly 50 is moved upwardly in canister body 21, a negative pressure can form in the lower vacuum chamber 54. This negative pressure can make it difficult for the surgeon to raise the filtering material 62 towards the tissue harvesting port 24 and could influence filtration. By opening the valve 74 and equalizing the pressure between the upper vacuum chamber 52 and the lower vacuum chamber 54 the surgeon can more readily raise the filtering material 62 within the canister body 21 while also facilitating filtration.

Covering the open top of the canister body 21 can be a removable, self-sealing lid 30. The substantially flat lid 30 can include an outer flange 32 for mating with the outwardly projecting flange 58 of the canister body 21 to seal off the upper portion of the upper vacuum chamber 52. The lid 30 further provides access to the vacuum connector 34 and tissue retrieval port 36 which allow admission directly into the upper vacuum chamber 52. The lid 30 can be formed in one-piece with the canister body 21.

The fluid evacuation port 22 is arranged in fluid communication with a lower portion of the lower vacuum chamber 54. This lower location is below the height of the filtering material 62. An evacuation tube can be slip fit onto or into the fluid evacuation port 22 or otherwise be suitably secured to the port 22. The fluid evacuation port 22, a tube, and a collection syringe 500 can be used to evacuate or drain tumescent fluids, oils, bloods, anesthetics, and other unwanted bilge fluids from the lower vacuum chamber 54 under suction from the syringe or other vacuum source.

The tissue harvesting port 24 is arranged in fluid communication with the upper vacuum chamber 52. In use, the location of the tissue harvesting port 24 is above the height of the filtering material 62 to allow the filtered pure fat that has accumulated on the upper vacuum chamber 52 side of the filtering material 62 to enter the tissue harvesting port 24 and be atraumatically removed from the canister device 20. An evacuation tube can be slip fit onto or into the tissue harvesting port 24 or otherwise be suitably secured to the port 24. The tissue harvesting port 24, a tube, and an adipose tissue collection syringe 400 can be used to collect the filtered pure fat from the upper vacuum chamber 52 of the tissue separating device 100.

The adipose tissue collection syringe 400 can be a conventional syringe with a hollow housing defining a collection chamber having an entry channel on one end that can attach to a tube for enabling collection of the filtered pure fat from port 24. After the collection syringe 400 collects a quantity of filtered pure fat from the tissue separating device 100, the syringe can be used to re-inject the filtered fat into a patient site for fat grafting or into another syringe body. Any collection syringe capacities can be implemented depending on the procedure being performed and the quantity of filtered fat is required as would be appreciated by one of ordinary skill in the art.

As best shown in FIGS. 2 and 3, the canister device 20 can be releasably secured to a holding tray 82. For example, the canister body 21 can include tabs 26 that allow a snap-connection with the holding tray 82 via flexible tangs 84. However, the canister device 20 can be secured to the holding tray 82 using any type of releasable connection mechanism as would be appreciated by one of ordinary skill in the art.

To promote the removal of filtered pure fat from the canister device 20 into the adipose tissue collection syringe 400, the holding tray 82 can be pivotally arranged on a base support 90. This pivoting structure allows the surgeon to tilt the canister device 20 so that the filtered pure fat can slide on the filtering material 62 towards and through the tissue harvesting port 24. The pivoting capability of the canister device 20 along with the height adjustability of the filtering material 62 helps the surgeon facilitate the removal of the filtered pure fat without directly manipulating the fat.

The pivoting capability of the canister device 20 also helps the surgeon facilitate the removal of the aqueous fluid component of the fatty liposuction aspirate from the lower vacuum chamber 54 through the tissue retrieval port 36.

As best shown in FIG. 3, the pivoting structure can include a pair of pivot pins 86 formed on the holding tray 82 that can engage with slots 92 formed in the base support 90 to allow the canister device 20 to be tilted in a forward and backward direction. However, the pivoting structure can include any structure that allows pivoting movement of the canister device 20 as would be appreciated by one of ordinary skill in the art. The fluid evacuation port 22 and the tissue harvesting port 24 can each be arranged on the canister body 20 in a location orthogonal to the pivot pins 86 of the holding tray 82 to allow the most efficient removal of the filtered pure fat and the aqueous fluid component of the fatty liposuction aspirate.

In use, the lid 30 can be removed by the surgeon and an optional fluid bath, such as a sterile saline solution, can be poured into the canister body 21 to a desired level. It can be preferable to ensure a ratio of the fluid bath to the desired amount of aspirated adipose tissue to allow the fatty tissue to float thereby initiating the separation process. Other treatments such as antibiotics and/or sterile tissue washing and separation fluids can also be introduced at this time or later on in the process as the surgeon determines. Such refining fluids can be introduced to wash, separate, and treat the aspirated adipose tissue.

At this point, the vacuum connector 34 can be placed in communication with the vacuum source 200 and the tissue retrieval port 36 can be placed in communication with the harvesting device 300. The tissue harvesting port 24 can be coupled to the adipose tissue collection syringe 400 and can be closed off by a pinch clamp. Similarly, the fluid evacuation port 22 can be coupled to a collection syringe 500 or other collection mechanism and can be closed off by a pinch clamp.

The vacuum source 200 can be turned on by the surgeon and the pump allowed to build to a suitable vacuum pressure to perform the fatty tissue harvesting process with the harvesting device 300 using conventional harvesting techniques. With the vacuum source 200 activated, a vacuum pressure relative to the ambient pressure can be generated and maintained in the upper vacuum chamber 52. A vacuum pressure range of 15-20 inches Hg has been found suitable to maintain a sufficient suction force in the upper vacuum chamber 52 to provide sufficient suction to the harvesting device 300 for aspirating adipose tissue from a patient and into the canister device 20.

Using conventional liposuction techniques, the cannula of the harvesting device 300 can be inserted into a patient site and a quantity of adipose tissue harvested under vacuum. The fatty liposuction aspirate will travel through the fat harvesting tube and is directed through the tissue retrieval port 36 and fall into the fluid bath or onto the filtering material 62 in the upper vacuum chamber 40. As commonly occurs during the adipose tissue aspiration process, other fluids and tissues such as blood, anesthetic, collagen strands, infiltrated tumescent fluids, oils, and other non-fatty tissues and fluids may be aspirated along with the fatty tissue. It will be appreciated that the process of separating the fatty tissue from other fluids and non-fatty tissue and fluids begins immediately.

While the fatty tissue can initially sink as it is introduced into the fluid bath, the more buoyant fatty tissue tends to rise within the fluid bath and will ultimately float at or near the upper water line of the fluid bath. It will be appreciated that pre-loading the canister device 20 with a fluid bath can cushion the entry of the fatty tissue into the canister thus reducing the trauma to the tissue as well as irrigating the tissue. As the fluid bath mixes with the aspirated, adipose tissue, it becomes bilge fluid that can later be evacuated further on in the procedure.

Once enough aspirated, adipose tissue is collected as determined by the surgeon to complete the transplantation or re-injection procedure, the vacuum source 200 can be left on at the same pressure or at a reduced pressure. However, it is preferable to turn off the vacuum source 200 while the fatty liposuction aspirate sits on the filtering material 62 and/or in the fluid bath for a short time interval to allow the separation process to proceed.

During the separation process, the filtered fatty tissue is prevented from entering the lower vacuum chamber 54 due to the size of the perforations in the filtering material 62. In addition, as the fatty tissue tends to float on the fluid bath, it is unlikely to block the perforations of the filtering material 62.

The fluid, including both saline bath and non-fatty tissues and other fluids collected from the patient during the harvesting procedure, passes from the upper vacuum chamber 52 and through the perforations in the filtering material 62, thereby accumulating in the lower vacuum chamber 54. The fluid that has accumulated in the lower vacuum chamber 54 can be evacuated through the fluid evacuation port 22 via a tube and into a collection syringe 500 or other collection mechanism.

The filtered pure fat that settles onto the filtering material 62 is separated and rinsed all within the sterile closed environment of the canister device 20. The filtered pure fat is heavily concentrated and ready for re-introduction into the patient as previously discussed above. However, after these washing and separation steps, other treatment additives can be added and repeated one or more times to further refine the fatty tissue.

The surgeon can open the pinch clamp downstream from the tissue harvesting port 24, tilt the canister device 20, and draw back the syringe plunger on the adipose tissue collection syringe 400. This places the collection syringe 400 in more efficient communication with the filtered pure fat that has collected on top of the filtering material 62. The tilting of the canister device 20 gently slopes the filtering material 62 to help provide a fat retrieval chute that directs the filtered pure fat to the collection syringe 400.

If more than one collection syringe is needed, the primary syringe can be uncoupled and additional syringes as needed may be coupled to the tubing end and the collection process repeated to load one or more syringes with filtered pure fat for re-injection.

The collection syringe 400 loaded with filtered pure fat can then be coupled to a desired cannula by the surgeon, and the filtered pure fat re-injected into the patient site using conventional autologous fatty tissue re-injection techniques.

The tissue separating device 100 of the present teachings allows the collection of filtered pure fat from aspirated adipose tissue without opening the canister device 20 and manipulating the fat. The tissue separating device 100 also minimizes the number of steps required by a surgeon to harvest, refine, and collect the filtered pure fat prior to re-introduction into the patient site. Trauma to the tissue, commonly caused by the use of a centrifuge, rougher manipulation of the tissue and the tissue container as commonly occurs when directing the tissue against a solid surface, and extending the time of the tissue outside the patient is significantly reduced, all while maintaining a sterile environment. The tissue separating device 100 of the present teachings can be easily integrated with conventional off the shelf waste canisters, vacuum sources, syringes, and harvesting devices.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A tissue separating device comprising:
    a canister device including canister body having a sidewall defining a volume;
    a tissue retrieval port arranged on the canister device and capable of being arranged in fluid communication with a harvesting device for directing a fatty liposuction aspirate into the volume of the canister device;
    a single adjustable height filtration assembly arranged within the canister body and including a filtering material separating the volume into an upper vacuum chamber and a lower vacuum chamber such that the fatty liposuction aspirate is directed by the tissue retrieval port into the upper vacuum chamber;
    a tissue harvesting port arranged in the sidewall of the canister body and capable of being arranged in communication with a collection device to allow the tissue harvesting port to atraumatically receive a filtered pure fat collected on the filtering material within the upper vacuum chamber; and
    an air pressure equalizing line operatively mounted to the canister device to allow fluid connection between the upper vacuum chamber and the lower vacuum chamber;
    wherein the filtration assembly is movably arranged within the canister body such that the filtering material is adjustable with respect to the tissue harvesting port as air pressure is equalized between the upper vacuum chamber and the lower vacuum chamber via the air pressure equalization line to alleviate a negative pressure in the lower vacuum chamber when the filtering material becomes clogged.

2. The tissue separating device of claim 1, further including a valve arranged in the air pressure equalizing line capable of selectively controlling the fluid connection between the upper vacuum chamber and the lower vacuum chamber.

3. The tissue separating device of claim 2, wherein the valve is a stop cock.

4. The tissue separating device of claim 2, further including an electrical controller capable of selectively controlling the valve arranged in the air pressure equalizing line to control the fluid connection between the upper vacuum chamber and the lower vacuum chamber.

5. The tissue separating device of claim 4, wherein the electrical controller selectively controls the valve based on pressure readings from at least one of the upper vacuum chamber and the lower vacuum chamber.

6. A tissue separating device comprising:
    a canister device including canister body having a sidewall defining a volume;
    an adjustable height filtration assembly arranged within the canister body and including a filtering material having a top side portion and a bottom side portion, the filtering material separating the volume into an upper vacuum chamber and a lower vacuum chamber;
    a tissue retrieval port arranged on the canister device and capable of being arranged in fluid communication with a harvesting device for directing a fatty liposuction aspirate into the-volume of the canister device onto the top side portion of the filtering material;
    an air pressure equalizing line operatively mounted to the canister device to allow fluid connection between the upper vacuum chamber and the lower vacuum chamber; and
    a tissue harvesting port arranged in the sidewall of the canister body and capable of being arranged in communication with a collection device for atraumatically receiving a filtered pure fat component collected on the top side portion of the filtering material;
    wherein the adjustable height filtration assembly is movably arranged within the canister body such that the filtering material is adjustable with respect to the tissue harvesting port as air pressure is equalized between the upper vacuum chamber and the lower vacuum chamber via the air pressure equalization line to alleviate a negative pressure in the lower vacuum chamber when the filtering material becomes clogged.

7. The tissue separating device of claim 6, further including a valve arranged in the air pressure equalizing line capable of selectively controlling the fluid connection between the upper vacuum chamber and the lower vacuum chamber.

8. The tissue separating device of claim 7, wherein the valve is a stop cock.

9. The tissue separating device of claim 7, further including an electrical controller capable of selectively controlling the valve arranged in the air pressure equalizing line to control the fluid connection between the upper vacuum chamber and the lower vacuum chamber.

10. The tissue separating device of claim 9, wherein the electrical controller selectively controls the valve based on pressure readings from at least one of the upper vacuum chamber and the lower vacuum chamber.

11. A tissue separating device comprising:
a canister device including canister body having a sidewall defining a volume;
a tissue retrieval port arranged on the canister device and capable of being arranged in fluid communication with a harvesting device for directing a fatty liposuction aspirate into the volume of the canister device;
a single adjustable height filtration assembly arranged within the canister body and including a filtering material separating the volume into an upper vacuum chamber and a lower vacuum chamber such that the fatty liposuction aspirate is directed by the tissue retrieval port into the upper vacuum chamber;
a tissue harvesting port arranged in the sidewall of the canister body and capable of being arranged in communication with a collection device to allow the tissue harvesting port to atraumatically receive a filtered pure fat collected on the filtering material within the upper vacuum chamber;
a vacuum connector for creating a vacuum in the upper vacuum chamber, wherein the vacuum connector and the tissue retrieval port are arranged on the same side of the filtering material so that vacuum is applied on the same side of the filtering material as the upper chamber; and
an air pressure equalizing line operatively mounted to the canister device to allow fluid connection between the upper vacuum chamber and the lower vacuum chamber as a height of the filtering material is adjusted with respect to the tissue harvesting port to alleviate a negative pressure in the lower vacuum chamber when the filtering material becomes clogged.

12. The tissue separating device of claim 11, further including a valve arranged in the air pressure equalizing line capable of selectively controlling the fluid connection between the upper vacuum chamber and the lower vacuum chamber.

13. The tissue separating device of claim 12, wherein the valve is a stop cock.

14. The tissue separating device of claim 12, further including an electrical controller capable of selectively controlling the valve arranged in the air pressure equalizing line to control the fluid connection between the upper vacuum chamber and the lower vacuum chamber.

15. The tissue separating device of claim 14, wherein the electrical controller selectively controls the valve based on pressure readings from at least one of the upper vacuum chamber and the lower vacuum chamber.

16. A method of separating pure fat from a fatty liposuction aspirate comprising:
providing a canister device defining a volume, the canister device including a tissue retrieval port, a filtration assembly including a filtering material having a top side portion and a bottom side portion and being movably arranged within the canister body, and a tissue harvesting port;
directing a fatty liposuction aspirate into the volume of the canister device and onto the top side portion of the filtering material of the filtration assembly;
separating the fatty liposuction aspirate using the filtering material into a filtered pure fat component collected on the top side portion of the filtering material and into an aqueous fluid component collected below the filtering material;
moving the filtering material with respect to the tissue harvesting port into a position to place the separated pure fat collected on the top side portion of the filtering material in communication with a collection device;
equalizing an air pressure between the upper vacuum chamber and the lower vacuum chamber as the filtering material is moved with respect to the tissue harvesting port to alleviate a negative pressure in the lower vacuum chamber when the filtering material becomes clogged; and
creating a vacuum at the tissue harvesting port using the collection device to atraumatically remove the filtered pure fat from the canister body without manipulating the fat.

17. The method of separating pure fat from a fatty liposuction aspirate of claim 16, further comprising tilting the canister device to promote the removal of the filtered pure fat from the canister body.

18. The method of separating pure fat from a fatty liposuction aspirate of claim 16, wherein equalizing an air pressure between the upper vacuum chamber and the lower vacuum chamber includes a valve capable of selectively controlling the air pressure between the upper vacuum chamber and the lower vacuum chamber.

19. The method of separating pure fat from a fatty liposuction aspirate of claim 18, wherein the valve is a stop cock.

20. The method of separating pure fat from a fatty liposuction aspirate of claim 18, further including an electrical controller capable of selectively controlling the valve.

* * * * *